(12) United States Patent
Todros et al.

(10) Patent No.: US 7,578,793 B2
(45) Date of Patent: Aug. 25, 2009

(54) SLEEP STAGING BASED ON CARDIO-RESPIRATORY SIGNALS

(75) Inventors: Koby Todros, Beer Sheva (IL); Amir Geva, Meitar (IL); Daniel Reisfeld, Tel-Aviv (IL)

(73) Assignee: Widemed Ltd., Herzlia (IL)

( * ) Notice: Subject to any disclaimer, the term of this patent is extended or adjusted under 35 U.S.C. 154(b) by 553 days.

(21) Appl. No.: 10/995,817

(22) Filed: Nov. 22, 2004

(65) Prior Publication Data

US 2006/0111635 A1 May 25, 2006

(51) Int. Cl.
*A61B 5/02* (2006.01)

(52) U.S. Cl. .................. 600/484; 600/300; 600/483

(58) Field of Classification Search .............. 600/300, 600/483, 484
See application file for complete search history.

(56) References Cited

U.S. PATENT DOCUMENTS

| | | | |
|---|---|---|---|
| 4,777,962 A | 10/1988 | Watson et al. | |
| 5,101,831 A | 4/1992 | Koyama et al. | |
| 5,187,657 A * | 2/1993 | Forbes ...................... | 600/513 |
| 5,280,791 A * | 1/1994 | Lavie ....................... | 600/509 |
| 5,803,066 A | 9/1998 | Rapoport et al. | |
| 5,819,007 A | 10/1998 | Elghazzawi | |
| 5,902,250 A * | 5/1999 | Verrier et al. ............. | 600/515 |
| 5,999,846 A | 12/1999 | Pardey et al. | |
| 6,070,098 A | 5/2000 | Moore-Ede et al. | |
| 6,142,950 A | 11/2000 | Allen et al. | |
| 6,223,064 B1 | 4/2001 | Lynn et al. | |
| 6,375,623 B1 | 4/2002 | Gavriely | |
| 6,529,752 B2 | 3/2003 | Krausman et al. | |
| 6,549,804 B1 | 4/2003 | Osorio et al. | |
| 6,589,188 B1 | 7/2003 | Street et al. | |
| 6,839,581 B1 | 1/2005 | El-Solh et al. | |
| 6,881,192 B1 | 4/2005 | Park | |
| 7,160,252 B2 | 1/2007 | Cho et al. | |
| 7,324,845 B2 * | 1/2008 | Mietus et al. ............. | 600/513 |
| 2002/0002327 A1 | 1/2002 | Grant et al. | |
| 2003/0004652 A1 | 1/2003 | Brunner et al. | |
| 2004/0073098 A1 | 4/2004 | Geva et al. | |
| 2004/0193068 A1 | 9/2004 | Burton et al. | |
| 2005/0076908 A1 * | 4/2005 | Lee et al. .............. | 128/204.23 |
| 2005/0080349 A1 * | 4/2005 | Okada et al. ............. | 600/534 |
| 2005/0148893 A1 * | 7/2005 | Misczynski et al. ...... | 600/513 |
| 2005/0192508 A1 * | 9/2005 | Lange et al. ............. | 600/534 |
| 2006/0041201 A1 * | 2/2006 | Behbehani et al. ........ | 600/521 |
| 2007/0118054 A1 * | 5/2007 | Pinhas et al. ............. | 600/587 |

(Continued)

FOREIGN PATENT DOCUMENTS

WO  WO 03/057025  7/2003

OTHER PUBLICATIONS

Bodenstein et al. "Feature Extraction from the Electroencephalogram by Adaptive Segmentation", Proceedings of the IEEE, vol. 65, No. 5, May 1977.*

(Continued)

*Primary Examiner*—Patricia C. Mallari
*Assistant Examiner*—Karen E Toth

(57) ABSTRACT

A method for diagnosis of a sleep-related condition of a patient having a thorax. The method includes receiving physiological signals from sensors coupled to the thorax of the patient, and analyzing the physiological signals, independently of any electroencephalogram (EEG) or electro-oculogram (EOG) signals, in order to identify sleep stages of the patient.

46 Claims, 8 Drawing Sheets

U.S. PATENT DOCUMENTS

2007/0208269 A1     9/2007    Mumford et al.
2007/0239057 A1    10/2007    Pu et al.

OTHER PUBLICATIONS

Lempel et al., "A Universal Algorithm for Sequential Data Compression", IEEE Transactions on Information Theory, IT-23:3 (1977), pp. 337-349.

Akselrod et al., "Power Spectrum Analysis of Heart Rate Fluctuation: A Quantitative Probe of Beat-to-Beat Cardiovascular Control", Science 213 (1981), pp. 220-222.

Eamonn Keogh, et al., "An Online Algorithm for Segmenting Time Series", pp. 289-296, 2001.

Penzel, et al, "Computer Based Sleep Recording and Analysis", Sleep Medicine Reviews 4:2 (2000), pp. 131-148.

Tesler, et al, "Can One Detect Sleep Stage Transitions for On-Line Sleep Scoring by Monitoring the Heart Rate Variability?" Somnologie 8 (2004), pp. 33-41.

A.K. Jain, et al, "Data Clustering: A Review", ACM Computing Surveys, vol. 31, No. 3, Sep. 1999.

http://www.sleepdisorderchannel.net, 2004.

M.G. Terzano, et al, "Atlas, rules, and recording techniques for the scoring of cyclic alternating pattern (CAP) in human sleep", Sleep Medicine 2 (2001), pp. 537-553.

ISR for PCT/IL07/01092 Mailed Jul. 23, 2008.

* cited by examiner

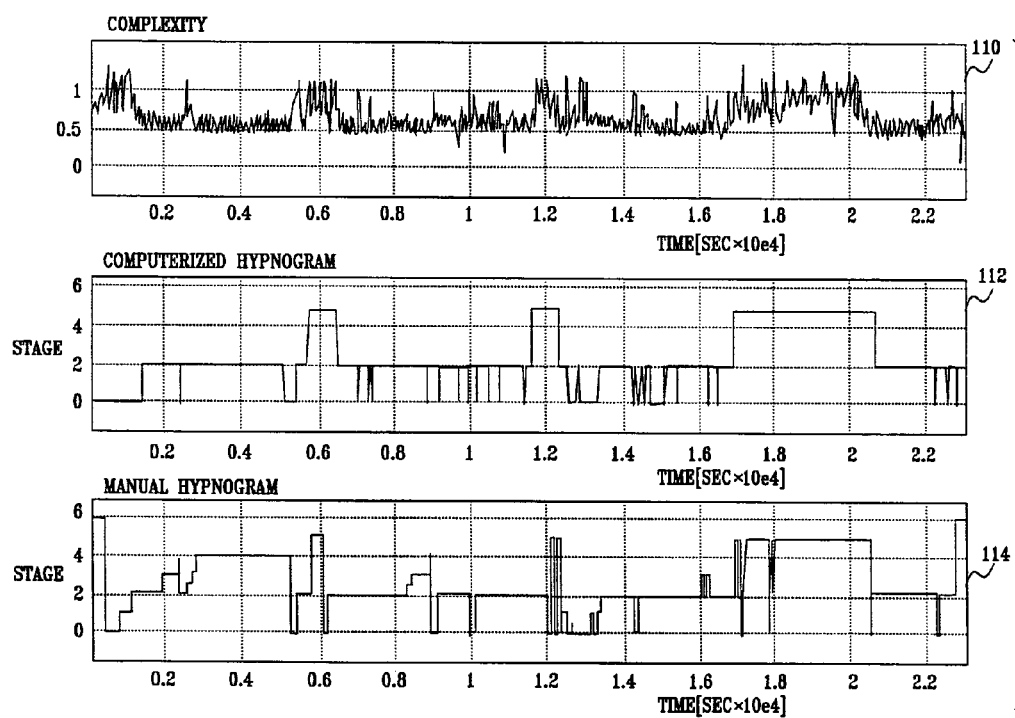

SLEEP STAGING BASED ON CARDIO-RESPIRATORY SIGNALS

CROSS-REFERENCE TO RELATED APPLICATION

This application is related to U.S. patent application Ser. No. 10/677,176, filed Oct. 2, 2003 (published as US 2004/0073098 A1), and to PCT Patent Application PCT/IL2004/000412, filed May 15, 2003. Both of these applications are assigned to the assignee of the present patent application, and their disclosures are incorporated herein by reference.

FIELD OF THE INVENTION

The present invention relates generally to physiological monitoring and diagnosis, and specifically to sleep recording and analysis.

BACKGROUND OF THE INVENTION

Human sleep is generally described as a succession of five recurring stages (plus waking, which is sometimes classified as a sixth stage). Sleep stages are typically monitored using a polysomnograph to collect physiological signals from the sleeping subject, including brain waves (EEG), eye movements (EOG), muscle activity (EMG), heartbeat (ECG), blood oxygen levels (SpO2) and respiration. The commonly-recognized stages include:
- Stage 1 sleep, or drowsiness. The eyes are closed during Stage 1 sleep, but if aroused from it, a person may feel as if he or she has not slept.
- Stage 2 is a period of light sleep, during which the body prepares to enter deep sleep.
- Stages 3 and 4 are deep sleep stages, with Stage 4 being more intense than Stage 3.
- Stage 5, REM (rapid eye movement) sleep, is distinguishable from non-REM (NREM) sleep by changes in physiological states, including its characteristic rapid eye movements.

Polysomnograms show brain wave patterns in REM to be similar to Stage 1 sleep. In normal sleep, heart rate and respiration speed up and become erratic, while the muscles may twitch. Intense dreaming occurs during REM sleep, but paralysis occurs simultaneously in the major voluntary muscle groups.

Although sleep staging is most often performed by a human operator, who reads and scores the polysomnogram, there are also methods known in the art for computerized sleep staging. Penzel et al review such methods in "Computer Based Sleep Recording and Analysis," *Sleep Medicine Reviews* 4:2 (2000), pages 131-148, which is incorporated herein by reference. According to this article, the minimum requirements for digital polysomnography as a basis for automatic sleep scoring include measurement of EEG, EOG and EMG, along with respiratory, cardiovascular and movement-related parameters.

Although automated sleep-staging is typically based primarily on analysis of the EEG signal, ECG analysis is frequently used along with the EEG to provide complementary information. For example, Telser et al. describe a method for detecting sleep transitions using ECG signals in "Can One Detect Sleep Stage Transitions for On-Line Sleep Scoring by Monitoring the Heart Rate Variability?" *Somnologie* 8 (2004), pages 33-41, which is incorporated herein by reference. The authors state that analysis of heart rate variability (HRV) can be used to distinguish NREM sleep from REM and wakefulness, but cannot distinguish between wakefulness and REM.

SUMMARY OF THE INVENTION

Embodiments of the present invention provide novel methods and systems for automated sleep staging, without dependence on electroencephalogram (EEG) or electro-oculogram (EOG) signals. In these embodiments, sleep staging is based on physiological signals provided by sensors that are coupled to the patient's thorax. Typically, these signals indicate the heart rate and/or respiration rate. The signals are analyzed automatically in order to distinguish between wakefulness, REM sleep and NREM sleep, and possibly between light NREM and deep NREM sleep, as well.

Although EEG monitoring may be considered the "gold standard" of sleep staging, it is cumbersome, uncomfortable and difficult to perform. Therefore, sleep studies are usually performed in a sleep lab or other dedicated facility with EEG capabilities. The methods of the present invention alleviate the need for EEG monitoring in many cases. Therefore, in some embodiments, the principles of the present invention are implemented in a bedside sleep monitoring system, which may be used to collect signals from the patient's thorax during sleep in a home or hospital ward environment. The signals may be analyzed to determine the patient's sleep staging in situ, or they may alternatively be transmitted over a communication network for remote analysis. Alternatively or additionally, the methods of analysis described herein may be used in conjunction with a Holter monitoring system or with the telemetry capabilities of an implanted device, such as a pacemaker or intracardiac defibrillator (ICD).

In other embodiments, signal processing methods taught by the present invention may be used in conjunction with EEG and other monitoring modalities.

There is therefore provided, in accordance with an embodiment of the present invention, a method for diagnosis of a sleep-related condition of a patient having a thorax, the method including:

receiving physiological signals from sensors coupled to the thorax of the patient; and analyzing the physiological signals, independently of any electroencephalogram (EEG) or electro-oculogram (EOG) signals, in order to identify sleep stages of the patient.

In disclosed embodiments, analyzing the physiological signals includes detecting motion of the patient based on at least one of the physiological signals. Typically, the at least one of the physiological signals includes at least one of an electrocardiogram (ECG) signal and a respiration signal.

In some of these embodiments, detecting the motion includes measuring an energy of the at least one of the physiological signals in a selected frequency band as a function of time, finding a respective characteristic of the energy in each of a plurality of time segments, and determining the patient to have moved during one or more of the time segments responsively to the respective variance. Typically, finding the respective characteristic includes finding a respective variance of each of the time segments. Additionally or alternatively, finding the respective characteristic includes performing an adaptive segmentation in order to identify the time segments such that the energy of the at least one of the signals is quasi-stationary during each of the time segments.

Typically, analyzing the physiological signals includes distinguishing, responsively to detecting the motion, between a waking stage and a REM sleep stage.

In some embodiments, analyzing the physiological signals includes performing an adaptive segmentation of at least one of the signals so as to identify time segments in which a characteristic of the at least one of the signals is quasi-stationary, and based on the adaptive segmentation, identifying transient events during which the characteristic of the at least one of the signals is not quasi-stationary. In one embodiment, analyzing the physiological signals includes determining at least one of the sleep stages to have been disturbed by occurrence of the transient events during the at least one of the sleep stages.

In disclosed embodiments, receiving the physiological signals includes receiving an electrocardiogram (ECG) signal. In some of these embodiments, analyzing the physiological signals includes measuring a variability of a heart rate of the patient responsively to the ECG signal, and identifying at least one of the sleep stages based on the variability. In one embodiment, identifying the at least one of the sleep stages includes computing a variance associated with the variability of the heart rate, and finding, responsively to the variance, a period during which the heart rate was decoupled from a respiratory function of the patient. Typically, identifying the period includes classifying the period as a REM sleep period.

Additionally or alternatively, identifying the at least one of the sleep stages includes measuring first and second energies respectively contained in first and second frequency bands of the variability of the heart rate during a selected epoch, and classifying the sleep stages responsively to a function of the first and second energies. Typically, the function includes a ratio of the first and second energies. In one embodiment, the first and second frequency bands respectively include low and high frequency bands, and classifying the sleep stages includes distinguishing between light and deep sleep stages based on the function.

In another aspect of the invention, receiving the physiological includes receiving a respiration signal, and analyzing the physiological signals includes analyzing the respiration signal together with the ECG signal in order to identify the sleep stages. Alternatively, the method may include receiving a respiration signal from an airway of the patient, wherein analyzing the physiological signals includes analyzing the respiration signal together with the ECG signal in order to identify the sleep stages.

In some embodiments, receiving the physiological signals includes receiving a respiration signal. In a disclosed embodiment, analyzing the physiological signals includes evaluating a complexity of the respiration signal during a selected epoch, and identifying at least one of the sleep stages responsively to the complexity. Typically, evaluating the complexity includes quantizing and compressing the respiration signal, and measuring the complexity based on an efficiency of compression of the quantized respiration signal. Additionally or alternatively, identifying the at least one of the sleep states includes determining the patient to be in NREM sleep if the complexity is below a predetermined threshold.

In a disclosed embodiment, receiving the physiological signals includes collecting the physiological signals at a bedside of the patient, and analyzing the physiological signals includes transmitting the physiological signals over a communication network for processing by a diagnostic processor remote from the bedside.

In alternative embodiments, receiving the physiological signals includes collecting the physiological signals from a Holter monitor coupled to the patient, or collecting the physiological signals from a device implanted in the thorax of the patient.

There is also provided, in accordance with an embodiment of the present invention, a method for diagnosis of a sleep-related condition of a patient, the method including:

receiving at least one of an electrocardiogram (ECG) signal and a respiration signal from a sensor coupled to the patient during sleep;

measuring an energy of the at least one of the ECG and respiration signals in a selected frequency band as a function of time;

finding a respective characteristic of the energy in each of a plurality of time segments; and determining the patient to have moved during one or more of the time segments responsively to the respective variance.

Typically, the respective characteristic includes a respective variance of the energy.

In disclosed embodiments, the method includes identifying a sleep stage of the patient during the one or more of the time segments responsively to determining the patient to have moved, wherein identifying the sleep stage includes distinguishing a REM sleep stage from a waking stage.

In an alternative embodiment, the method includes receiving an electroencephalogram (EEG) signal from the patient, wherein identifying the sleep stage includes processing the EEG signal together with the at least one of the ECG and respiration signals.

There is additionally provided, in accordance with an embodiment of the present invention, a method for diagnosis of a sleep-related condition of a patient, the method including:

receiving an electrocardiogram (ECG) signal from a sensor coupled to the patient during sleep;

measuring a variability of a heart rate of the patient responsively to the ECG signal;

computing a characteristic of the variability of the heart rate; and finding, responsively to the variance, a period during which the heart rate was decoupled from a respiratory function of the patient.

Typically, the characteristic includes a variance associated with the variability of the heart rate.

There is further provided, in accordance with an embodiment of the present invention, a method for diagnosis of a sleep-related condition of a patient, the method including:

receiving a respiration signal from a sensor coupled to the patient during sleep;

evaluating a complexity of the respiration signal during a selected epoch; and identifying a sleep stage of the patient responsively to the complexity.

In a disclosed embodiment, evaluating the complexity includes quantizing and compressing the respiration signal, and measuring the complexity based on an efficiency of compression of the quantized respiration signal. Typically, identifying the sleep stage includes determining the patient to be in NREM sleep if the complexity is below a predetermined threshold.

In an alternative embodiment, the method includes receiving an electroencephalogram (EEG) signal from the patient, wherein identifying the sleep stage includes processing the EEG signal together with the respiration signal.

There is moreover provided, in accordance with an embodiment of the present invention, apparatus for diagnosis of a sleep-related condition of a patient having a thorax, the apparatus including:

one or more sensors, coupled to the thorax of the patient, which are adapted to receive physiological signals; and a diagnostic processor, which is coupled to receive and process the physiological signals, independently of any electroencephalogram (EEG) or electro-oculogram (EOG) signals, in order to identify sleep stages of the patient.

In a disclosed embodiment, the apparatus includes a console, which is coupled to collect the physiological signals at a bedside of the patient, and to transmit the physiological signals over a communication network for processing by the diagnostic processor at a location remote from the bedside.

There is furthermore provided, in accordance with an embodiment of the present invention, apparatus for diagnosis of a sleep-related condition of a patient, the apparatus including:

a sensor, which is adapted to be coupled to the patient during sleep so as to receive from the patient at least one of an electrocardiogram (ECG) signal and a respiration signal; and a diagnostic processor, which is coupled to measure an energy of the at least one of the ECG and respiration signals in a selected frequency band as a function of time, to find a respective characteristic of the energy in each of a plurality of time segments, and to determine the patient to have moved during one or more of the time segments responsively to the respective variance.

There is also provided, in accordance with an embodiment of the present invention, apparatus for diagnosis of a sleep-related condition of a patient, the apparatus including:

one or more electrodes, which are adapted to receive an electrocardiogram (ECG) signal from the patient during sleep; and a diagnostic processor, which is coupled to measure a variability of a heart rate of the patient responsively to the ECG signal, to compute a characteristic of the variability of the heart rate, and to find, responsively to the variance, a period during which the heart rate was decoupled from a respiratory function of the patient.

There is additionally provided, in accordance with an embodiment of the present invention, apparatus for diagnosis of a sleep-related condition of a patient, the apparatus including:

a respiration sensor, which is adapted to receive a respiration signal from the patient during sleep; and a diagnostic processor, which is coupled to evaluate a complexity of the respiration signal during a selected epoch, and to identify a sleep stage of the patient responsively to the complexity.

There is further provided, in accordance with an embodiment of the present invention, a computer software product for diagnosis of a sleep-related condition of a patient having a thorax, the product including a computer-readable medium, in which program instructions are stored, which instructions, when read by a computer, cause the computer to receive physiological signals from one or more sensors coupled to the thorax of the patient during sleep, and to process the physiological signals, independently of any electroencephalogram (EEG) or electro-oculogram (EOG) signals, in order to identify sleep stages of the patient.

There is moreover provided, in accordance with an embodiment of the present invention, a computer software product for diagnosis of a sleep-related condition of a patient, the product including a computer-readable medium, in which program instructions are stored, which instructions, when read by a computer, cause the computer to receive from the patient at least one of an electrocardiogram (ECG) signal and a respiration signal during sleep, and to measure an energy of the at least one of the ECG and respiration signals in a selected frequency band as a function of time, to find a respective variance of the energy in each of a plurality of time segments, and to determine the patient to have moved during one or more of the time segments responsively to the respective variance.

There is also provided, in accordance with an embodiment of the present invention, a computer software product for diagnosis of a sleep-related condition of a patient, the product including a computer-readable medium, in which program instructions are stored, which instructions, when read by a computer, cause the computer to receive an electrocardiogram (ECG) signal from the patient during sleep, and to measure a variability of a heart rate of the patient responsively to the ECG signal, to compute a variance associated with the variability of the heart rate, and to find, responsively to the variance, a period during which the heart rate was decoupled from a respiratory function of the patient.

There is additionally provided, in accordance with an embodiment of the present invention, a computer software product for diagnosis of a sleep-related condition of a patient, the product including a computer-readable medium, in which program instructions are stored, which instructions, when read by a computer, cause the computer to receive a respiration signal from the patient during sleep, and to evaluate a complexity of the respiration signal during a selected epoch, and to identify a sleep stage of the patient responsively to the complexity.

The present invention will be more fully understood from the following detailed description of the embodiments thereof, taken together with the drawings in which:

BRIEF DESCRIPTION OF THE DRAWINGS

FIG. 8 is a schematic plot that schematically illustrates a complexity analysis of a thoracic signal and a hypnogram derived therefrom, in accordance with an embodiment of the present invention.

DETAILED DESCRIPTION OF EMBODIMENTS

Figure 1:
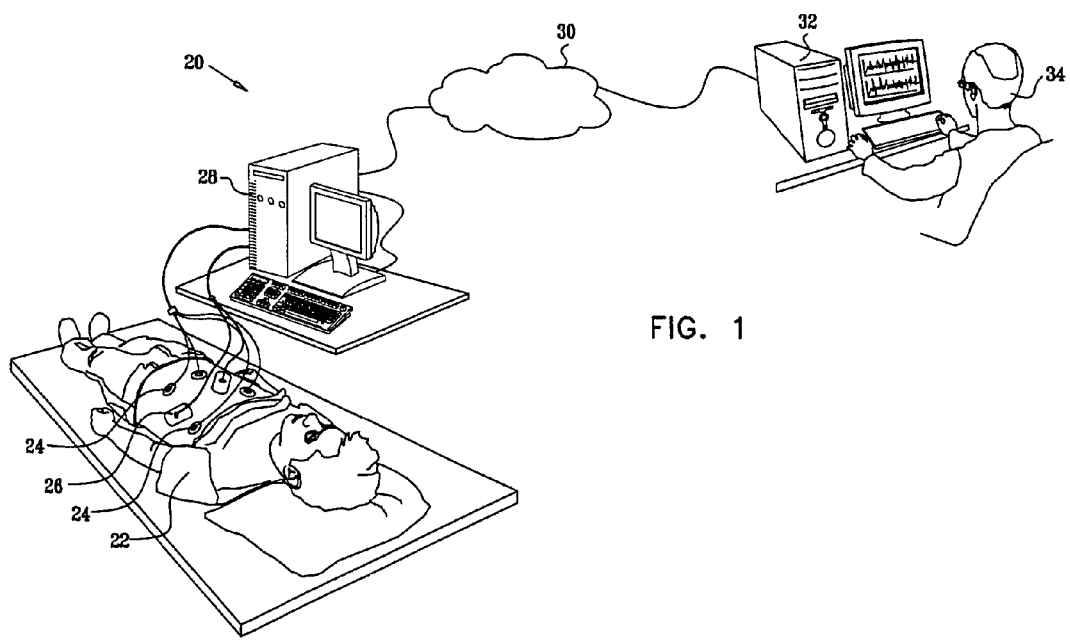
FIG. 1 is a schematic, pictorial illustration of a system for sleep monitoring, in accordance with an embodiment of the present invention.

FIG. 1 is a schematic, pictorial illustration of a system 20 for sleep monitoring and diagnosis, in accordance with an embodiment of the present invention. In this embodiment, system 20 is used to monitor a patient 22 in a home or hospital ward environment, although the principles of the present invention may similarly be applied in dedicated sleep laboratories. System 20 receives and analyzes physiological signals generated by the patient's body, including an ECG signal measured by skin electrodes 24 and a respiration signal measured by a respiration sensor 26. The signals are collected, amplified and digitized by a console 28. No EEG or EOG electrodes are required on the patient's head in system 20, although the techniques of ECG and respiration monitoring and analysis that are described herein may alternatively be combined with EEG, EOG and other sleep monitoring modalities that are known in the art.

Respiration sensor 26 typically makes electrical measurements of thoracic and abdominal movement. For example, sensor 26 may comprise two or more skin electrodes, which are driven by console 28 to make a plethysmographic measurement of the change in impedance or inductance between the electrodes as a result of the patient's respiratory effort. (It is also possible to use the ECG electrodes for this purpose.) Alternatively, the respiration sensor may comprise a belt, which is placed around the patient's chest or abdomen and senses changes in the body perimeter. Additionally or alternatively, air flow measurement may be used for respiration sensing. For example, the air flow from the patient's nose and/or mouth may be measured using a pressure cannula, thermistor, or CO2 sensor. Any other suitable respiration sensor known in the art may also be used, in addition to or instead of the above sensor types.

Additionally or alternatively, console 28 may gather signals from an existing set of sensors coupled to patient 22. For example, while patient 22 is undergoing Holter monitoring, as is known in the art, the monitored physiological signals may also be used for sleep staging, as described hereinbelow. As another example, implantable cardiac devices, such as pacemakers and ICDs, typically sense the patient's ECG and are capable of transmitting telemetry signals out to a suitable receiver. Such implantable devices sometimes include motion sensors, as well, such as an accelerometer, whose output may also be used, along with the ECG, in sleep staging. Additionally or alternatively, the implantable device may generate and transmit impedance-based respiration measurements (known in the art as "minute ventilation").

Console 28 may process and analyze the ECG and respiration signals locally, using the methods described hereinbelow. In the present embodiment, however, console 28 is coupled to communicate over a network 30, such as a telephone network or the Internet, with a diagnostic processor 32. This configuration permits sleep studies to be performed simultaneously in multiple different locations. Processor 32 typically comprises a general-purpose computer with suitable software for carrying out the functions described herein. This software may be downloaded to processor 32 in electronic form, or it may alternatively be provided on tangible media, such as optical, magnetic or non-volatile electronic memory. Processor 32 analyzes the signals conveyed by console 28 in order to identify sleep stages of patient 22 and to display the results of the analysis to an operator 34, such as a physician.

Figure 7:
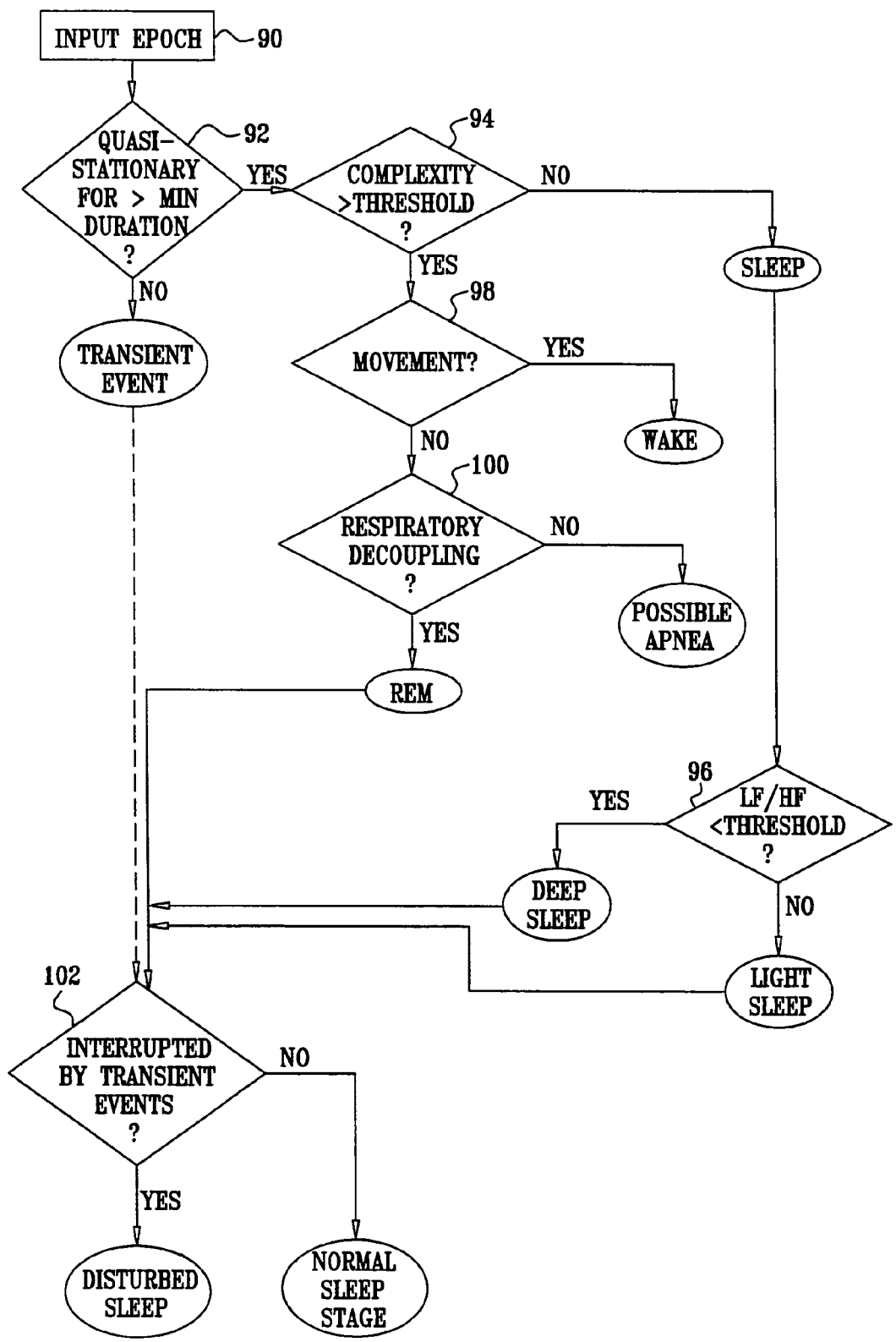
FIG. 7 is a flow chart that schematically illustrates a method for automated sleep staging, in accordance with an embodiment of the present invention.

Typically, processor 32 identifies sleep stages based on a combination of different analyses that are applied to the signals received from patient 22. An exemplary multi-parameter sleep staging method is shown in FIG. 7 and is described hereinbelow with reference thereto. Before describing this combined method, however, a number of the specific analyses that may be used in the method will first be explained.

Figure 2:
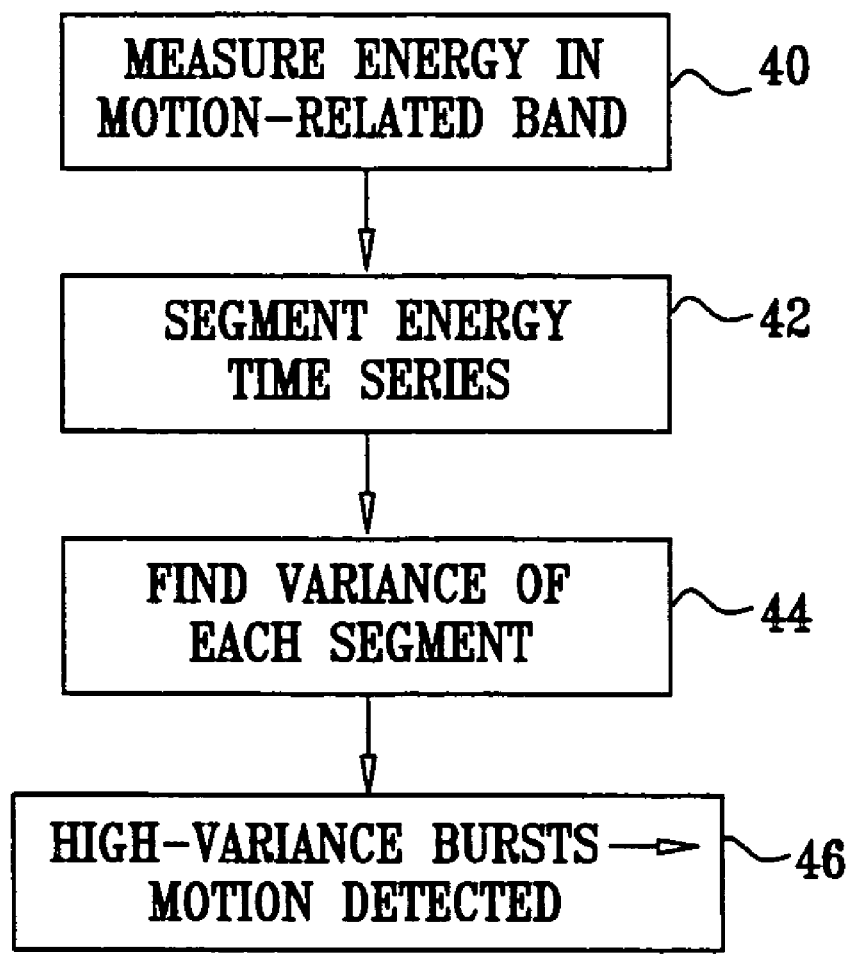
FIG. 2 is a flow chart that schematically illustrates a method for processing physiological signals, in accordance with an embodiment of the present invention.

FIG. 2 is a flow chart that schematically illustrates a method for detecting motion of patient 22 based on ECG measurements made using electrodes 24, in accordance with an embodiment of the present invention. This motion measurement may be used to distinguish between REM (in which the voluntary muscles are paralyzed) and other states. No dedicated motion sensor is required.

The method of FIG. 2 is based on measuring the energy content of motion-related frequency bands in the ECG signal, at an energy measurement step 40. The inventors have found that the ECG "noise bands," below 2 Hz and above 20 Hz, can be used for this purpose. Alternatively or additionally, other bands that contain motion information may be used. To perform the energy measurement, processor 32 divides the ECG signal into overlapping segments $S_i$, each $\delta$ seconds long, with the starting times of successive segments spaced $\epsilon$ seconds apart. Typically, $\delta=5$, and $\epsilon=0.5$, but other values of these parameters, larger or smaller, may alternatively be used. The noise measure for each segment i is given by:

$$\eta_i = \frac{E_i(0, 2) + E_i\left(20, \frac{F_s}{2}\right)}{E_i\left(0, \frac{F_s}{2}\right)} \quad (1)$$

wherein $E_i$ is the integrated energy in the range [x,y] (in Hz), and $F_s$ is the sampling rate. An AR (autoregressive) spectrum offers an efficient, accurate means for frequency estimation for short data segments. The inventors have used it for computing the ECG power spectrum and found that for an ECG sampling rate of 100 Hz, using four AR coefficients gives satisfactory results.

Processor 32 assembles the noise energy values $\eta_i$ as a time series with a spacing of $\epsilon$ seconds between series elements. The processor may apply spline interpolation, typically with a cubic spline, to interpolate series values between these measured values. For example, the noise energy may initially be computed with 2 Hz resolution, followed by cubic spline fitting to give a continuous noise signal, and concluding with resampling of the continuous noise signal at 6 Hz.

The processor then divides the time series into new segments $R_j$ by an adaptive segmentation process, at a segmentation step 42. Methods of adaptive segmentation that may be applied to physiological signals (particularly in the context of sleep analysis) are described in detail in the above-mentioned PCT Patent Application PCT/IL2004/000412. Briefly, the adaptive segmentation process divides the time series into segments, each of which is characterized by quasi-stationary behavior. "Quasi-stationary" means that certain statistical properties of each segment, such as spectral amplitude variations, are contained within predefined bounds Those segments of the time series that are not quasi-stationary over at least a predefined minimum duration may be identified as transient events.

In one embodiment, processor 32 uses a procedure to define and segment quasi-stationary segments based on a similarity measure D as follows: Let $A=\{a_1 \ldots a_n\}$ and $B=\{b_1 \ldots b_m\}$ be two segments of length n and m respectively. Let $\sigma_A, \sigma_B$ be the standard deviations of A and B, respectively, and let $\sigma_{AB}$ be the standard deviation of the concatenation of A and B. Segments A and B are considered similar if:

$$D(A, B) = \frac{\sigma_A^n \sigma_B^m}{\sigma_{AB}^{n+m}} < T \quad (2)$$

wherein T is a predefined threshold. Other similarity measures may alternatively be used, for example, log D(A, B). Now, taking 2l to be the minimal length of a quasi-stationary segment (typically 2l>5 sec), and $X=\{x_1, x_2, \ldots\}$ to be the series to be segmented, and denoting the segment $\{x_i, \ldots, x_j\}$ as [i,j], the segmentation procedure at step 42 is expressed as follows:

Initially i=1;

While (signal is not fully segmented) {
   Look for min j≧i such that [j,j+l] and
     [j+l+1,j+2l] are similar
   If (j>i) {
     [i,j−1] is a non-stationary segment;
     i=j}
   Else {
     Look for max j>i+l such that [i,j] and
       [j+1,j+l] are similar
     [i,j+l] is a quasi-stationary segment;
     i=j+l+1;}}

Processor 32 next computes the statistical variance of the energy values in each segment $R_j$, at a variance computation step 44. The variance of each segment is compared to those of its neighboring segments, at a burst detection step 46. If the variance ratio between the neighboring segments is greater than a predetermined threshold, processor 32 concludes that patient 22 moved during the high-variance segment. Typically, the processor compares the noise measure of each segment to that of the closest preceding and subsequent segments that are of at least a predetermined minimum length (typically at least 60 sec). If the noise measure in a given segment is at least 15 times greater than these preceding and succeeding segments, the patient is considered to have moved during the segment. Alternatively, other characteristics of the energy may be used, such as the entropy.

Figure 3:
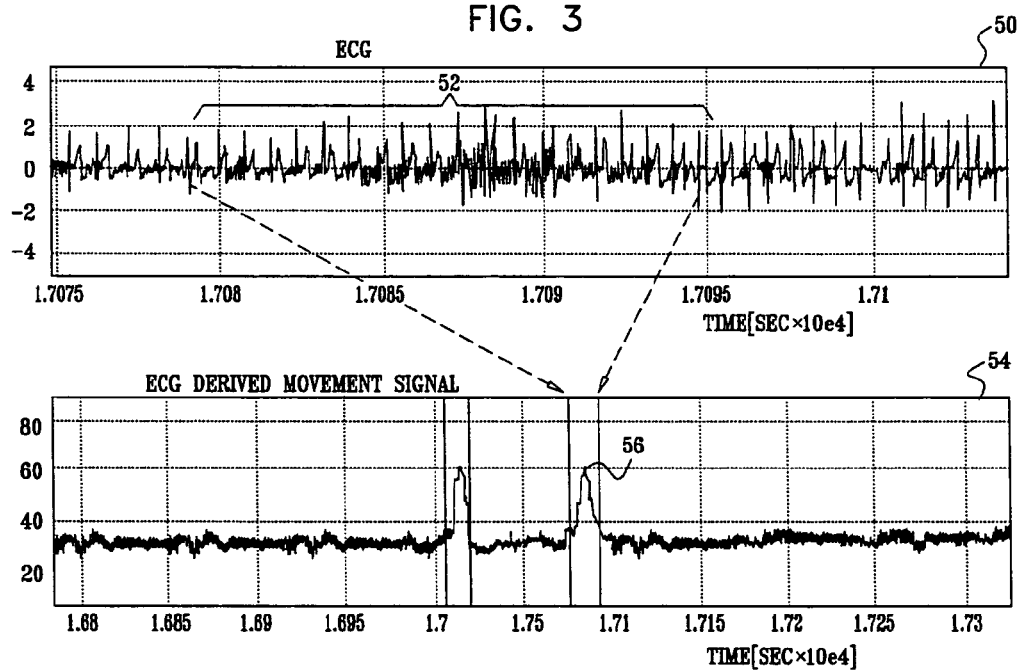
FIG. 3 is a schematic plot of an ECG signal and of a movement signal derived therefrom, in accordance with an embodiment of the present invention.

FIG. 3 is a schematic plot showing an ECG signal and a movement signal derived therefrom, in accordance with an embodiment of the present invention. An upper plot 50 shows the ECG signal taken from a patient during sleep. The signal includes a number of quasi-stationary segments 52 with relatively high variance. A lower plot 54 shows the movement signal derived from the ECG (on a condensed time scale) Segments 52 are reflected in a peak 56 appearing in the movement signal. Processor 32 records this peak as an indication that patient 22 moved during the time frame in question.

The method of FIG. 2 may similarly be applied to detect patient movement based on respiration signals. In this case, at step 40, the high-frequency component of the respiration signal is considered to contain the motion information. Typically, the energy is measured in a high-pass band above 1.5 Hz. An energy time series is thus created, as described above, and adaptively segmented at step 42. The variance of each segment in the energy series is computed at step 44, and high-variance bursts are detected at step 46. Let σ be the variance of a segment S, and let $\sigma_l, \sigma_r$ be the variances of previous and succeeding neighboring segments (of sufficient length). The segment S is considered a burst if max $$\left(\frac{\sigma}{\sigma_l}, \frac{\sigma}{\sigma_r}\right) > T.$$

Typically, a segment meeting this criterion with T=5 is regarded as indicative of patient motion, as long as the neighboring segments are at least 10 sec long.

Figure 4:
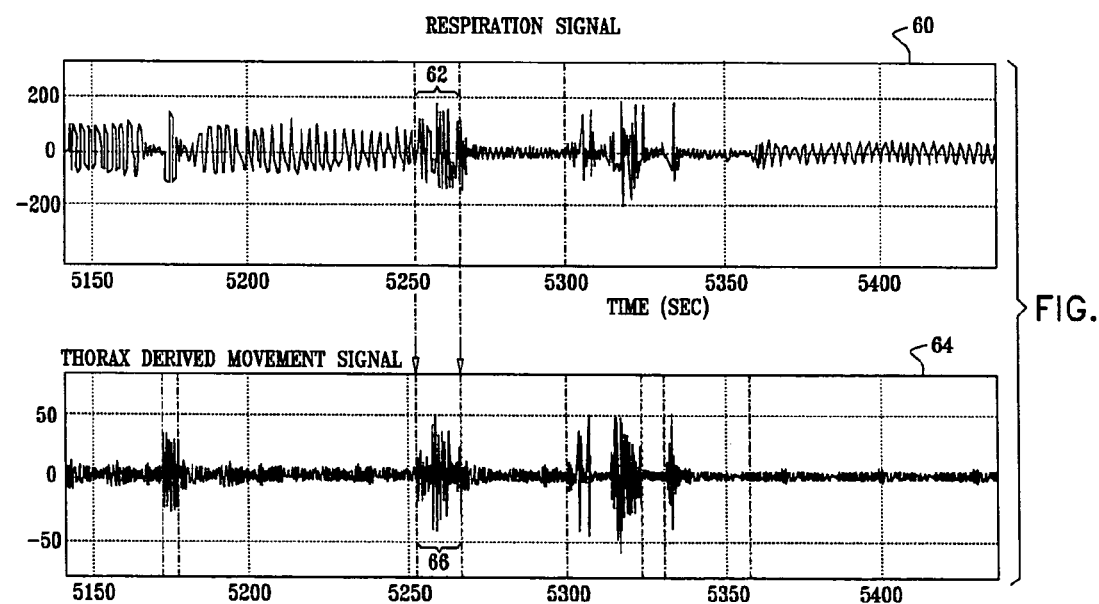
FIG. 4 is a schematic plot of a respiration signal and of a movement signal derived therefrom, in accordance with another embodiment of the present invention.

FIG. 4 is a schematic plot showing a respiration signal and a movement signal derived therefrom, in accordance with another embodiment of the present invention. An upper plot 60 shows the actual respiration signal, including a high-variance segment 62. The corresponding motion signal is shown in a lower plot 64. The high variance of segment 62 is evident in a corresponding segment 66 in the motion signal, indicating that patient motion occurred during this segment.

Figure 5:
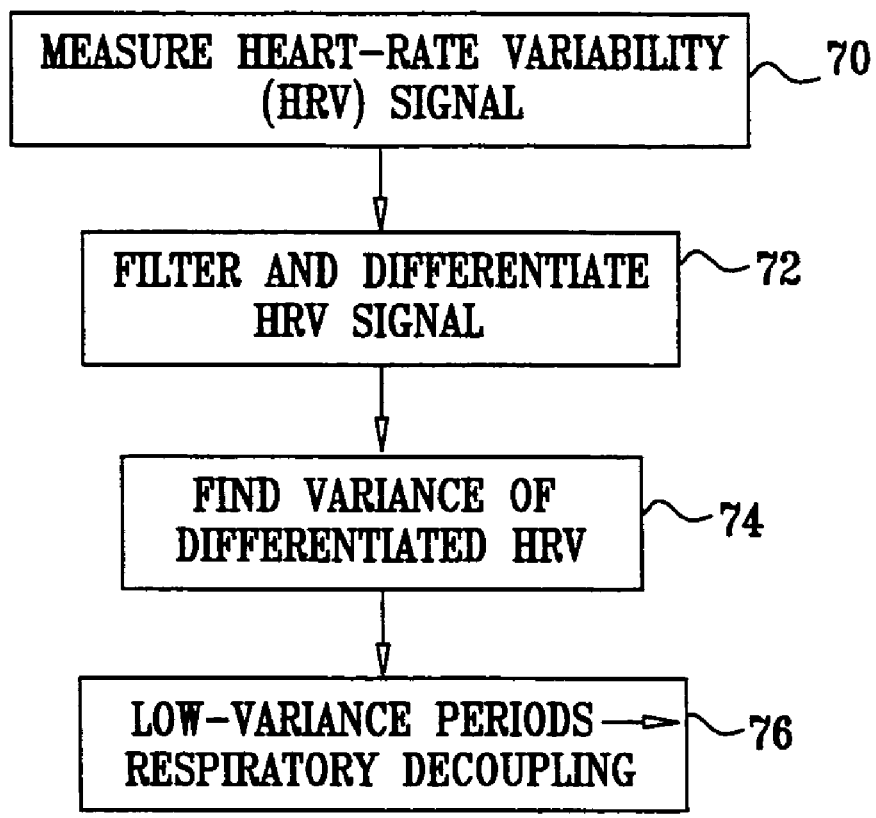
FIG. 5 is a flow chart that schematically illustrates a method for processing a heart-rate variability (HRV) signal, in accordance with an embodiment of the present invention.
Figure 6:
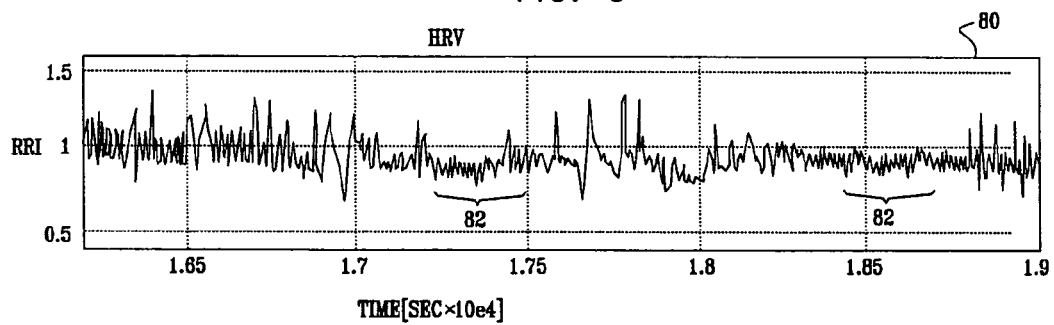
FIG. 6 is a schematic plot illustrating a variance analysis of a HRV signal, in accordance with an embodiment of the present invention.

Reference is now made to FIGS. 5 and 6, which schematically illustrate a method for detecting respiratory decoupling in a heart rate variability (HRV) signal, in accordance with an embodiment of the present invention. This method is based on the observation that during NREM sleep, the heart rate varies, typically in synchronization with the patient's respiration. In REM, however, the heart rate is decoupled from respiration, i.e., it fails to exhibit the variation characteristic of NREM sleep. FIG. 5 is a flow chart showing the steps in the present method, while FIG. 6 shows a plot 80 of a HRV signal to which the method is applied. HRV is expressed and plotted in terms of the length (in seconds) of the R-R interval (RRI) in the ECG signal.

Processor 32 processes the ECG signal received from electrodes 24 to detect the R waves and thus measure the HRV, at a HRV measurement step 70. The processor then filters the HRV signal that it has derived, at a HRV processing step 72. Typically, at this step, the processor uses a bandpass filter with a passband corresponding to the respiratory frequency range, for example, 0.15 to 0.4 Hz. The processor then calculates the second derivative of the filtered HRV signal. It calculates the variance of this second derivative signal, at a variance computation step 74. Typically, the variance is computed over a series of overlapping time frames, for example, 30 sec time frames with starting times spaced 1 sec apart.

Processor 32 analyzes the time sequence of variance values to identify periods of low variance, at a variance analysis step 76. Typically, for this purpose, the processor uses a hierarchical clustering algorithm to divide the time sequence into segments. In other words, the processor recursively partitions the time sequence into smaller and smaller segments until it finds a period or periods whose variance is lower than the neighboring periods by a predetermined ratio, or until it reaches a minimal segment length. Let $\sigma_A$ be the variance of a segment of length n, let $\sigma_B$ be the variance of a neighboring segment of length m, and let $\sigma_{AB}$ be the variance of the concatenated segment. As noted earlier, the two segments may be considered similar if $$\log \frac{\sigma_A^n \sigma_B^m}{\sigma_{AB}^{n+m}} < T.$$

The similarity threshold, T, for identifying a low variance segment is typically 15, i.e., similarity in excess of this threshold indicates that respiratory decoupling occurred during this segment. Low-variance segments 82 of this sort, indicative of respiratory decoupling, can be seen in FIG. 6.

Additionally or alternatively, processor 32 may compute the complexity of the respiration signal measured by respiration sensor 26. NREM sleep is known to be characterized by even breathing, i.e., low-complexity respiration signals, while waking and REM typically have more complex, irregular breathing patterns. Various methods may be used to calculate a measure of signal complexity.

In an exemplary embodiment, processor 32 divides the signal into time segments, and finds the mean m and the standard deviation σ for each segment. Each segment is typically 30 sec long, and the time offset between consecutive segments is typically 1 sec. The processor then uses the values m and σ to quantize the respiration signal s in each segment into n levels, for example, n=4:

$$s = \begin{cases} `a' & x \geq m + \sigma \\ `b' & m + \sigma > x \geq m \\ `c' & m > x > m - \sigma \\ `d' & m \leq m - \sigma \end{cases} \quad (3)$$

To measure the complexity of each segment, the processor compresses the string of quantized signal values in the segment using a complexity-dependent compression scheme. For example, the processor may use Lempel-Ziv compression, as described by Lempel et al., in "A Universal Algorithm for Sequential Data Compression," IEEE Transactions on Information Theory, IT-23:3 (1977), pages 337-349. The signal complexity may be defined in terms of the compression efficiency ε:

$$\varepsilon = \frac{L \log_n N}{N} \quad (4)$$

wherein N is the length of the segment, and L is the length of the compressed string. A typical calculation of respiratory signal complexity over time is illustrated below in FIG. 8.

FIG. 7 is a flow chart that schematically illustrates a method for automated sleep staging using the signal processing techniques described above, in accordance with an embodiment of the present invention. In this sleep staging process, processor 32 analyzes the ECG and respiration data in epochs of 30 sec each, at an epoch input step 90. This period is chosen because it is the standard epoch length used in manual sleep staging.

The processor determines whether the ECG and respiratory signals were quasi-stationary (as defined above) within the current epoch, at a stationarity evaluation step 92. If quasi-stationarity was not maintained for at least a minimal, predetermined length of time (typically 5 sec) in the epoch, then the processor notes the possible occurrence of a transient event. The processor may further analyze this transient event to identify short-term variations in the patient's sleep state, such as micro-arousals. The processing and significance of transient events are further described in the above-mentioned PCT Patent Application PCT/IL2004/000412.

Assuming the signals to have been quasi-stationary in the epoch under analysis, processor 32 next computes the complexity of the respiratory signal, at a complexity evaluation step 94. The method of computation is described above. If the average complexity over the epoch is less than a predetermined threshold, for example, 0.6, then the patient is determined to be in NREM sleep.

Optionally, the frequency content of the ECG signal may be evaluated in order to determine the depth of NREM sleep, at a frequency assessment step 96. It has been found that a low range of HRV frequencies (in the 0.04-0.15 Hz range, referred to hereinbelow as the LF range) is associated with baroreflex sympathetic control, encountered in light sleep; while a higher range (0.15-0.4 Hz, referred to hereinbelow as the HF range) is associated with parasympathetic control, which is characteristic of deep sleep. Results of this sort are reported, for example, by Akselrod et al., in "Power Spectrum Analysis of Heart Rate Fluctuation: A Quantitative Probe of Beat-to-Beat Cardiovascular Control," Science 213 (1981), pages 220-222, which is incorporated herein be reference. Thus, at step 96, processor measures the energy contained in the LF and HF ranges of the HRV during the current epoch and computes the ratio of energies in the two bands, LF energy/HF energy. If the ratio is greater than a predetermined threshold, for example, 1.8, the patient is considered to be in light sleep, i.e., stage 1 or 2. Otherwise, the patient is considered to be in deep sleep, stage 3 or 4.

Returning now to step 94, if processor 32 finds the average complexity of the respiratory signal over the current epoch to be greater than the complexity threshold, the processor concludes that the patient is not in NREM sleep, and checks whether the patient has moved during this epoch or the preceding or succeeding epoch, at a movement checking step 98. Movement may be assessed, for example, by applying the method of FIG. 2 to ECG or respiration signals, as described above. If the patient is determined to have moved, the processor concludes that the patient is awake. Typically, average movement activity over 30 sec greater than 0.5, coupled with respiration signal complexity greater than 0.6, is indicative of a state of wakefulness.

If the patient is found at step 98 not to have moved during the current epoch, processor 32 checks the HRV signal for respiratory decoupling, at a decoupling detection step 100. Respiratory decoupling may be detected using the method described above with reference to FIG. 5. If the HRV variance, as defined above, is sufficiently low to qualify as decoupling, and is accompanied by an absence of movement, the processor then classifies the current epoch as REM sleep. If the HRV variance is not low, despite the lack of movement, processor 32 marks the current epoch as anomalous. Such anomalies may occur, for example, due to sleep apneas.

As noted above, processor 32 detects transient events in the ECG and/or respiratory signals at step 92. After classifying a given epoch as belonging to a REM or NREM sleep state, the processor checks the record of transient events to determine whether the patient's sleep in the current epoch has been interrupted by such events, at an interruption checking step 102. If the current epoch is uninterrupted, it is classified as normal sleep. If one or more transient events interrupted the current epoch, however, processor 32 notes that the quality of sleep during this epoch was disturbed. This information may be used in diagnosing certain pathological conditions affecting the quality of sleep of patient 22.

FIG. 8 is a schematic plot showing the results of sleep staging performed by processor 32, in accordance with an embodiment of the present invention. An upper plot 110 in the figure shows the results of a computation of complexity of the respiration signal received from sensor 26, as determined at step 94 (FIG. 7) and described above. A middle plot 112 is a hypnogram, generated automatically by processor 32 using the method of FIG. 7, and based on the complexity signal shown in plot 110, along with other respiratory and ECG data. The computer-generated hypnogram is compared with a hypnogram generated manually by an expert human scorer, which is shown in a lower plot 114.

In this embodiment, the LF/HF ratio (step 96) was not computed, and the processor was thus unable to distinguish between different stages of NREM sleep. Therefore, plot 112 shows only stages 0 (wakefulness), 2 (representing all NREM sleep stages) and 5 (REM sleep). With this reservation, there is still a good correlation between the sleep stages derived automatically, as shown in plot 112, and the manual scoring results shown in plot 114. As noted above, this result was achieved based on thoracic measurements only, without the use of EEG or EOG signals.

Although the embodiments described above rely only on measurements made using certain sensors on the patient's thorax, the principles of the present invention may similarly be applied to measurements of heart rate and respiration using sensors of other types and in other locations. The measurements and signal processing techniques taught by the present invention may also be combined with collection and processing of other physiological signals, including EEG and EOG. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for diagnosis of a sleep-related condition of a patient having a thorax, the method comprising:
   receiving physiological signals from sensors coupled to the thorax of the patient; and
   analyzing the physiological signals, independently of any electroencephalogram (EEG) or electro-oculogram (EOG) signals, in order to identify sleep stages of the patient, wherein analyzing the physiological signals comprises:
   performing an adaptive segmentation of at least one of the signals so as to identify time segments in which a characteristic of the at least one of the signals is quasi-stationary; and
   based on the adaptive segmentation, identifying transient events during which the characteristic of the at least one of the signals is not quasi-stationary.

2. The method according to claim 1, wherein analyzing the physiological signals comprises detecting motion of the patient based on at least one of the physiological signals.

3. The method according to claim 2, wherein the at least one of the physiological signals comprises at least one of an electrocardiogram (ECG) signal and a respiration signal.

4. The method according to claim 2, wherein analyzing the physiological signals comprises distinguishing, responsively to detecting the motion, between a waking stage and a REM sleep stage.

5. The method according to claim 1, wherein analyzing the physiological signals comprises determining at least one of the sleep stages to have been disturbed by occurrence of the transient events during the at least one of the sleep stages.

6. The method according to claim 1, wherein receiving the physiological signals comprises receiving an electrocardiogram (ECG) signal.

7. The method according to claim 6, wherein analyzing the physiological signals comprises measuring a variability of a heart rate of the patient responsively to the ECG signal, and identifying at least one of the sleep stages based on the variability.

8. The method according to claim 7, wherein identifying the at least one of the sleep stages comprises computing a variance associated with the variability of the heart rate, and finding, responsively to the variance, a period during which the heart rate was decoupled from a respiratory function of the patient.

9. The method according to claim 8, wherein identifying the period comprises classifying the period as a REM sleep period.

10. The method according to claim 7, wherein identifying the at least one of the sleep stages comprises measuring first and second energies respectively contained in first and second frequency bands of the variability of the heart rate during a selected epoch, and classifying the sleep stages responsively to a function of the first and second energies.

11. The method according to claim 10, wherein the function comprises a ratio of the first and second energies.

12. The method according to claim 10, wherein the first and second frequency bands respectively comprise low and high frequency bands, and wherein classifying the sleep stages comprises distinguishing between light and deep sleep stages based on the function.

13. The method according to claim 6, wherein receiving the physiological signals comprises receiving a respiration signal, and wherein analyzing the physiological signals comprises analyzing the respiration signal together with the ECG signal in order to identify the sleep stages.

14. The method according to claim 6, and comprising receiving a respiration signal from an airway of the patient, wherein analyzing the physiological signals comprises analyzing the respiration signal together with the ECG signal in order to identify the sleep stages.

15. The method according to claim 1, wherein receiving the physiological signals comprises receiving a respiration signal.

16. The method according to claim 15, wherein analyzing the physiological signals comprises evaluating a complexity of the respiration signal during a selected epoch, and identifying at least one of the sleep stages responsively to the complexity.

17. The method according to claim 16, wherein evaluating the complexity comprises quantizing and compressing the respiration signal, and measuring the complexity based on an efficiency of compression of the quantized respiration signal.

18. The method according to claim 16, wherein identifying the at least one of the sleep states comprises determining the patient to be in NREM sleep if the complexity is below a predetermined threshold.

19. The method according to claim 1, wherein receiving the physiological signals comprises collecting the physiological signals at a bedside of the patient, and wherein analyzing the physiological signals comprises transmitting the physiological signals over a communication network for processing by a diagnostic processor remote from the bedside.

20. The method according to claim 1, wherein receiving the physiological signals comprises collecting the physiological signals from a Holter monitor coupled to the patient.

21. The method according to claim 1, wherein receiving the physiological signals comprises collecting the physiological signals from a device implanted in the thorax of the patient.

22. Apparatus for diagnosis of a sleep-related condition of a patient having a thorax, the apparatus comprising:
   one or more sensors, adapted to be coupled to the thorax of the patient, which are adapted to receive physiological signals; and
   a diagnostic processor, which is coupled to receive and process the physiological signals, independently of any electroencephalogram (EEG) or electrooculogram CEOG) signals, in order to identify sleep stages of the patient,
   wherein the diagnostic processor is adapted to perform an adaptive segmentation of at least one of the signals so as to identify time segments in which a characteristic of the at least one of the signals is quasi-stationary, and based on the adaptive segmentation, to identify transient events during which the characteristic of the at least one of the signals is not quasi-stationary.

23. The apparatus according to claim 22, wherein the diagnostic processor is adapted to detect motion of the patient based on at least one of the physiological signals.

24. The apparatus according to claim 23, wherein the at least one of the physiological signals comprises at least one of an electrocardiogram (ECG) signal and a respiration signal.

25. The apparatus according to claim 23, wherein the diagnostic processor is adapted to distinguish, responsively to detecting the motion, between a waking stage and a REM sleep stage.

26. The apparatus according to claim 22, wherein the diagnostic processor is adapted to determine at least one of the sleep stages to have been disturbed by occurrence of the transient events during the at least one of the sleep stages.

27. The apparatus according to claim 22, wherein the physiological signals comprise an electrocardiogram (ECG) signal.

28. The apparatus according to claim 27, wherein the diagnostic processor is adapted to measure a variability of a heart rate of the patient responsively to the ECG signal, and to identify at least one of the sleep stages based on the variability.

29. The apparatus according to claim 28, wherein the diagnostic processor is adapted to compute a variance associated with the variability of the heart rate, and to find, responsively to the variance, a period during which the heart rate was decoupled from a respiratory function of the patient.

30. The apparatus according to claim 29, wherein the diagnostic processor is adapted to classify the period as a REM sleep period responsively to decoupling of the heart rate from the respiratory function.

31. The apparatus according to claim 28, wherein the diagnostic processor is adapted to measure first and second energies respectively contained in first and second frequency bands of the variability of the heart rate during a selected epoch, and to classify the sleep stages responsively to a function of the first and second energies.

32. The apparatus according to claim 31, wherein the function comprises a ratio of the first and second energies.

33. The apparatus according to claim 31, wherein the first and second frequency bands respectively comprise low and high frequency bands, and wherein the diagnostic processor is adapted to distinguish between light and deep sleep stages based on the function.

34. The apparatus according to claim 27, wherein the physiological signals comprise a respiration signal, and wherein the diagnostic processor is adapted to analyze the respiration signal together with the ECG signal in order to identify the sleep stages.

35. The apparatus according to claim 27, wherein the diagnostic processor is coupled to receive a respiration signal from an airway sensor in an airway of the patient, and wherein the diagnostic processor is adapted to analyze the respiration signal together with the ECG signal in order to identify the sleep stages.

36. The apparatus according to claim 22, wherein the physiological signals comprise a respiration signal.

37. The apparatus according to claim 36, wherein the diagnostic processor is adapted to evaluate a complexity of the respiration signal during a selected epoch, and to identify at least one of the sleep stages responsively to the complexity.

38. The apparatus according to claim 37, wherein the diagnostic processor is adapted to quantize and compress the respiration signal, and to measure the complexity based on an efficiency of compression of the quantized respiration signal.

39. The apparatus according to claim 37, wherein the diagnostic processor is adapted to determine the patient to be in NREM sleep if the complexity is below a predetermined threshold.

40. The apparatus according to claim 22, and comprising a console, which is coupled to collect the physiological signals at a bedside of the patient, and to transmit the physiological signals over a communication network for processing by the diagnostic processor at a location remote from the bedside.

41. The apparatus according to claim 22, wherein the diagnostic processor is coupled to receive the physiological signals from a Holter monitor coupled to the patient.

42. The apparatus according to claim 22, wherein the diagnostic processor is coupled to receive the physiological signals from a device implanted in the thorax of the patient.

43. A computer software product for diagnosis of a sleep-related condition of a patient having a thorax, the product comprising a computer-readable medium, in which program instructions are stored, which instructions, when read by a computer, cause the computer to receive physiological signals from one or more sensors coupled to the thorax of the patient during sleep, and to process the physiological signals, independently of any electroencephalogram (EEG) or electro-oculogram (EOG) signals, in order to identify sleep stages of the patient, wherein the instructions cause the computer to perform an adaptive segmentation of at least one of the signals so as to identify time segments in which a characteristic of the at least one of the signals is quasi-stationary, and based on the adaptive segmentation, to identify transient events during which the characteristic of the at least one of the signals is not quasi-stationary.

44. A computer software product for diagnosis of a sleep-related condition of a patient having a thorax, the product comprising a computer-readable medium, in which program instructions are stored, which instructions, when read by a computer, cause the computer to receive physiological signals from one or more sensors coupled to the thorax of the patient during sleep, and to process the physiological signals, independently of any electroencephalogram (EEG) or electrooculogram (EOG) signals, in order to identify sleep stages of the patient by performing an adaptive segmentation of at least one of the signals so as to identify time segments in which a characteristic of the at least one of the signals is quasi-stationary, and based on the adaptive segmentation, identifying transient events during which the characteristic of the at least one of the signals is not quasi-stationary.

45. A method for diagnosis of a sleep-related condition of a patient having a thorax, the method comprising:

receiving physiological signals from sensors coupled to the thorax of the patient; and analyzing the physiological signals, independently of any electroencephalogram (EEG) or electro-oculogram (EOG) signals, in order to identify sleep stages of the patient, wherein analyzing the physiological signals comprises detecting motion of the patient, other than respiratory motion, based on at least one of the physiological signals, and wherein detecting the motion comprises:

measuring an energy of the at least one of the physiological signals in a selected frequency band as a function of time;

finding a respective characteristic of the energy in each of a plurality of time segments; and determining the patient to have moved during one or more of the time segments responsively to the respective characteristic, and wherein finding the respective characteristic comprises performing an adaptive segmentation in order to identify the time segments such that the energy of the at least one of the signals is quasi-stationary during each of the time segments.

46. Apparatus for diagnosis of a sleep-related condition of a patient having a thorax, the apparatus comprising:

one or more sensors, adapted to be coupled to the thorax of the patient, which are adapted to receive physiological signals; and a diagnostic processor, which is coupled to receive and process the physiological signals, independently of any electroencephalogram (EEG) or electro-oculogram (EOG) signals, in order to identify sleep stages of the patient wherein the diagnostic processor is adapted to detect motion of the patient, other than respiratory motion, based on at least one of the physiological signals, and wherein the diagnostic processor is adapted to measure an energy of the at least one of the physiological signals in a selected frequency band as a function of time, to find a respective characteristic of the energy in each of a plurality of time segments, and to determine the patient to have moved during one or more of the time segments responsively to the respective characteristic, and wherein the diagnostic processor is operative to perform an adaptive segmentation in order to identify the time segments such that the energy of the at least one of the signals is quasi-stationary during each of the time segments.

* * * * *